(12) United States Patent
Gharpure et al.

(10) Patent No.: US 11,198,703 B2
(45) Date of Patent: Dec. 14, 2021

(54) PROCESS FOR THE PREPARATION OF SGLT2 INHIBITORS AND INTERMEDIATES THEREOF

(71) Applicant: PIRAMAL ENTERPRISES LIMITED, Mumbai (IN)

(72) Inventors: Milind Gharpure, Maharashtra (IN); Sanjay Kumar Sharma, Maharashtra (IN); Sandesh Vishwasrao, Maharashtra (IN); Prasad Vichare, Maharashtra (IN); Dipak Varal, Maharashtra (IN)

(73) Assignee: PIRAMAL ENTERPRISES LIMITED, Mumbai (IN)

( * ) Notice: Subject to any disclaimer, the term of this patent is extended or adjusted under 35 U.S.C. 154(b) by 0 days.

(21) Appl. No.: 16/612,028

(22) PCT Filed: May 9, 2018

(86) PCT No.: PCT/IB2018/053222
§ 371 (c)(1),
(2) Date: Nov. 8, 2019

(87) PCT Pub. No.: WO2018/207113
PCT Pub. Date: Nov. 15, 2018

(65) Prior Publication Data
US 2020/0123186 A1    Apr. 23, 2020

(30) Foreign Application Priority Data
May 9, 2017   (IN) .............................. 201721016263

(51) Int. Cl.
*C07H 7/04* (2006.01)
*C07H 1/00* (2006.01)
*C07H 1/06* (2006.01)
*C07H 7/06* (2006.01)

(52) U.S. Cl.
CPC ................. *C07H 7/04* (2013.01); *C07H 1/00* (2013.01); *C07H 1/06* (2013.01); *C07H 7/06* (2013.01)

(58) Field of Classification Search
None
See application file for complete search history.

(56) References Cited

U.S. PATENT DOCUMENTS

| | | | |
|---|---|---|---|
| 7,838,499 B2 | 11/2010 | Chen et al. | |
| 9,006,403 B2 | 4/2015 | Liou et al. | |
| 9,062,087 B2 | 6/2015 | Zhao et al. | |
| 2004/0138439 A1* | 7/2004 | Deshpande | ............ C07H 23/00 536/18.7 |

FOREIGN PATENT DOCUMENTS

| | | | |
|---|---|---|---|
| CN | 102234260 A | 11/2011 | |
| WO | 2009/026537 A1 | 2/2009 | |
| WO | 2010/022313 A2 | 2/2010 | |
| WO | 2013/152476 A1 | 10/2013 | |
| WO | 2013/152654 A | 10/2013 | |
| WO | WO-2016178148 A1 * | 11/2016 | ............. A61K 31/70 |

OTHER PUBLICATIONS

ISR for International Application No. PCT/IB2018/053220.
Written Opinion for International Application No. PCT/IB2018/053220.
CN 102234260 A _ Espacenet English Abstract.
Ge Xu, et al., "An efficient method for synthesis of bexagliflozin and its carbon-13 labeled analogue", Tetrahedron Letters, (20160000), vol. 57, pp. 4684-4687, XP029744253 [X] 9-12 * abstract; DOI: http://dx.doi.org/10.1016/j.tetlet.2016.09.003.

* cited by examiner

*Primary Examiner* — Layla D Berry
(74) *Attorney, Agent, or Firm* — Ladas & Parry LLP

(57) ABSTRACT

The present invention relates to an industrially feasible and economically viable process for preparation of Bexagliflozin of formula V in significantly high yield and purity.

Formula V

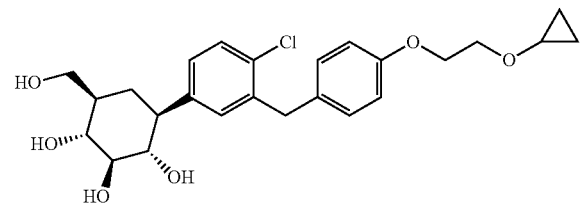

8 Claims, No Drawings

PROCESS FOR THE PREPARATION OF SGLT2 INHIBITORS AND INTERMEDIATES THEREOF

RELATED APPLICATION

This application is an application under 35 U.S.C. 371 of International Application No. PCT/IB2018/053222 filed on 9 May 2018, which claims priority from Indian Application No. 201721016263 filed 9 May 2017, the disclosures of which are incorporated in their entirety by reference herein.

FIELD OF THE INVENTION

The present invention relates to an improved process for the preparation of Bexagliflozin, (2S,3R,4R,5S,6R)-2-[4-chloro-3-[[4-(2-cyclopropyloxy ethoxy)phenyl]methyl]phenyl]-6-(hydroxymethyl)oxane-3,4,5-triol represented herein by compound of formula V, its salts, hydrates, solvates and its intermediates thereof.

BACKGROUND OF THE INVENTION

The following discussion of the prior art is intended to present the invention in an appropriate technical context, and allows its significance to be properly appreciated. Unless clearly indicated to the contrary, reference to any prior art in this specification should not be construed as an expressed or implied admission that such art is widely known or forms part of common general knowledge in the field.

Bexagliflozin (formula V), is an inhibitor of sodium-glucose co-transporter 2 (SGLT2), the compound is investigated in lowering hemoglobin Mc (HbA1c) levels in patients with type 2 diabetes mellitus (T2DM) and moderate renal impairment. The compound is for therapeutic intervention in diabetes and related disorders, SGLT2 is localized in the renal proximal tubule and is reportedly responsible for the majority of glucose reuptake by the kidneys. Bexagliflozin, the active ingredient is also chemically known as (2S,3R,4R,5S,6R)-2-[4-chloro-3-[[4-(2-cyclopropyloxy-ethoxy)phenyl]methyl]phenyl]-6-(hydroxymethyl)oxane-3,4,5-triol and is structurally represented as follows;

Formula V

Bexagliflozin being an important anti-diabetic drug used to improve glycemic control in people with type 2 diabetes; a number of processes for its preparation as well as for its intermediates are known in the art.

U.S. Pat. No. 7,838,499; which is hereby incorporated by reference, discloses Bexagliflozin as well as a process for the preparation of Bexagliflozin; as depicted below in Scheme-1:

Scheme-1

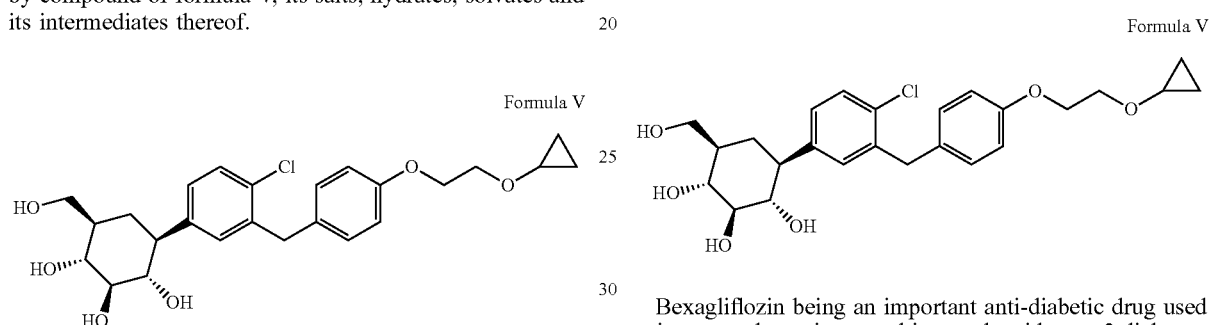

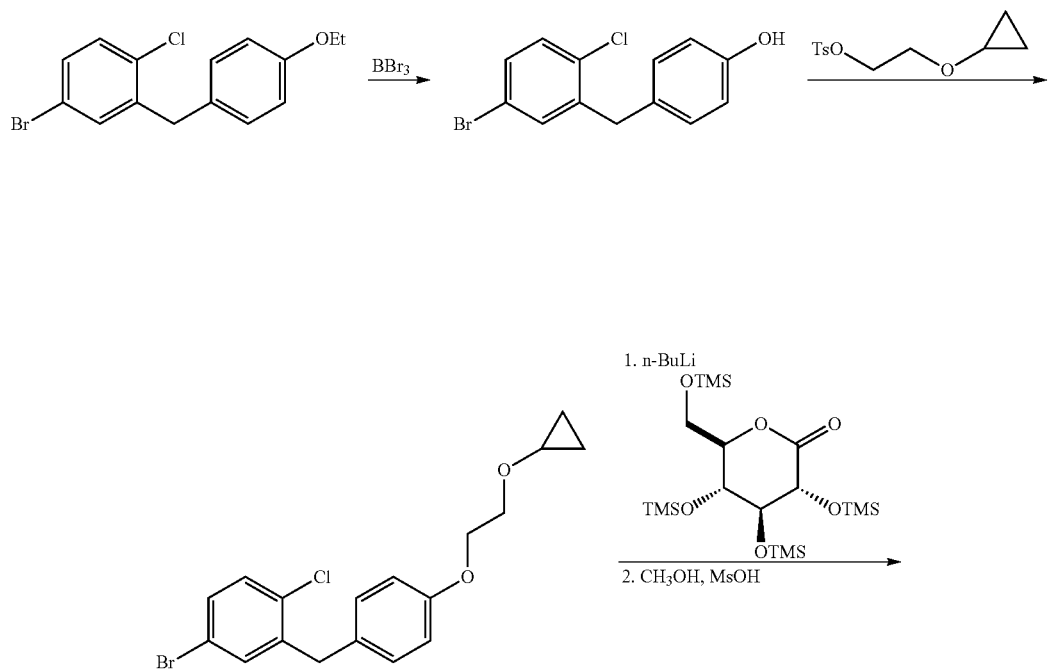

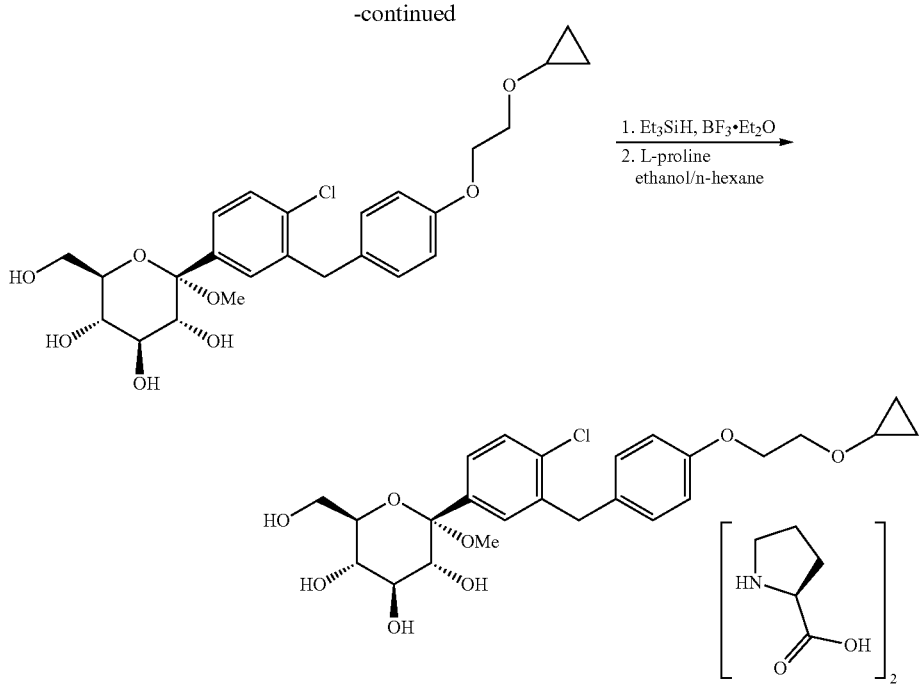

U.S. Pat. No. 9,006,403; which is hereby incorporated by reference, discloses crystalline form of (2S,3R,4R,5S,6R)-2-(4-chloro-3-(4-(2-cyclopropoxyethoxy) benzyl) phenyl)-6-(hydroxymethyl)tetrahydro-2H-pyran-3,4,5-triol, bis(L-proline) complex process for preparation thereof as depicted above in Scheme-1.

The PCT international publication WO 2013/152654 disclosed preparation of Bexagliflozin using turbo Grignard reagent; as depicted below in Scheme-2:

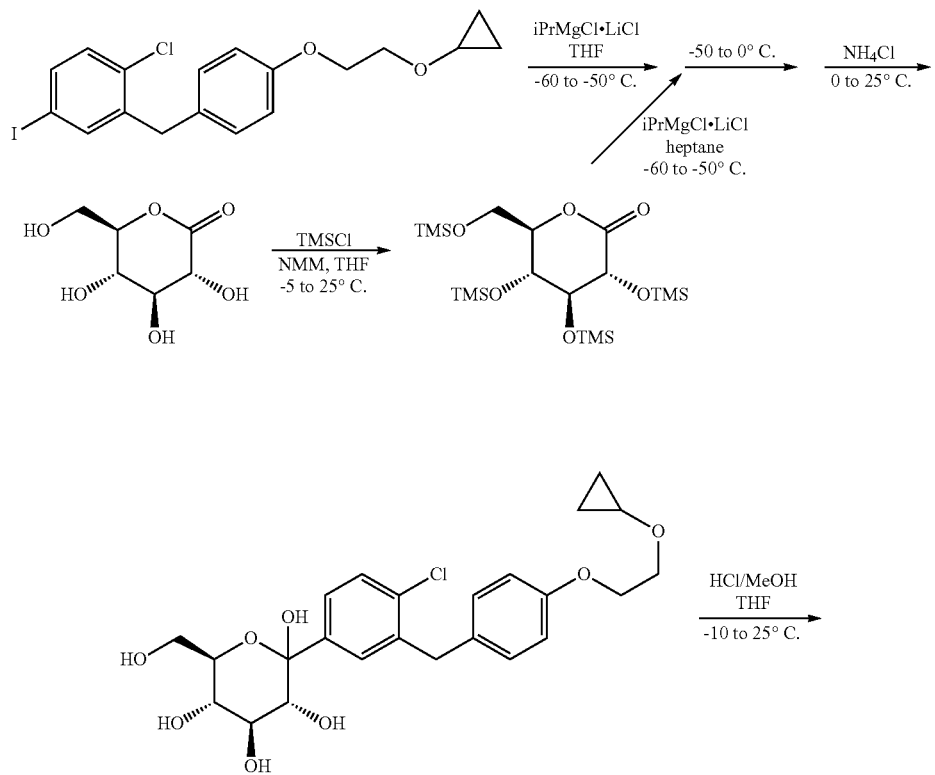

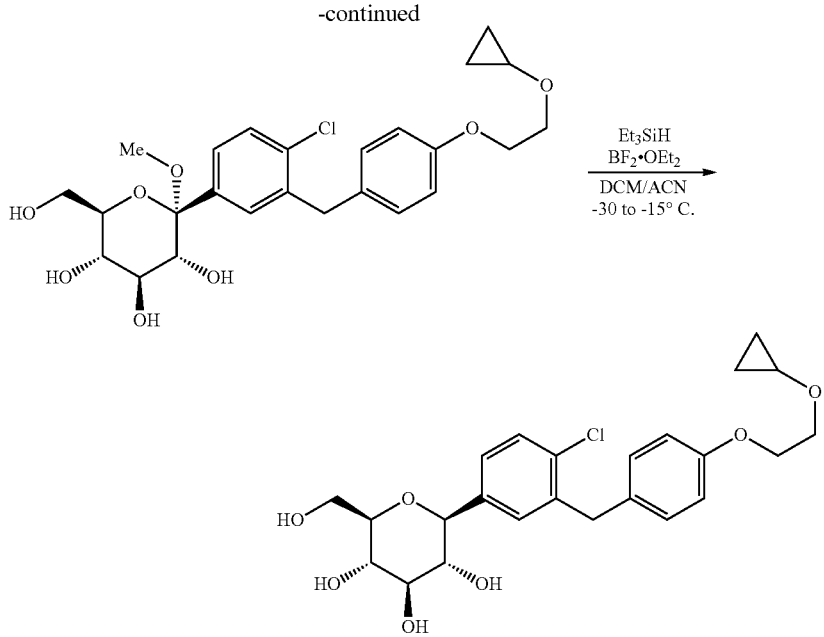
U.S. Pat. No. 9,062,087 B2 which is hereby incorporated by reference, discloses the preparation of compound as depicted below in Scheme-3:
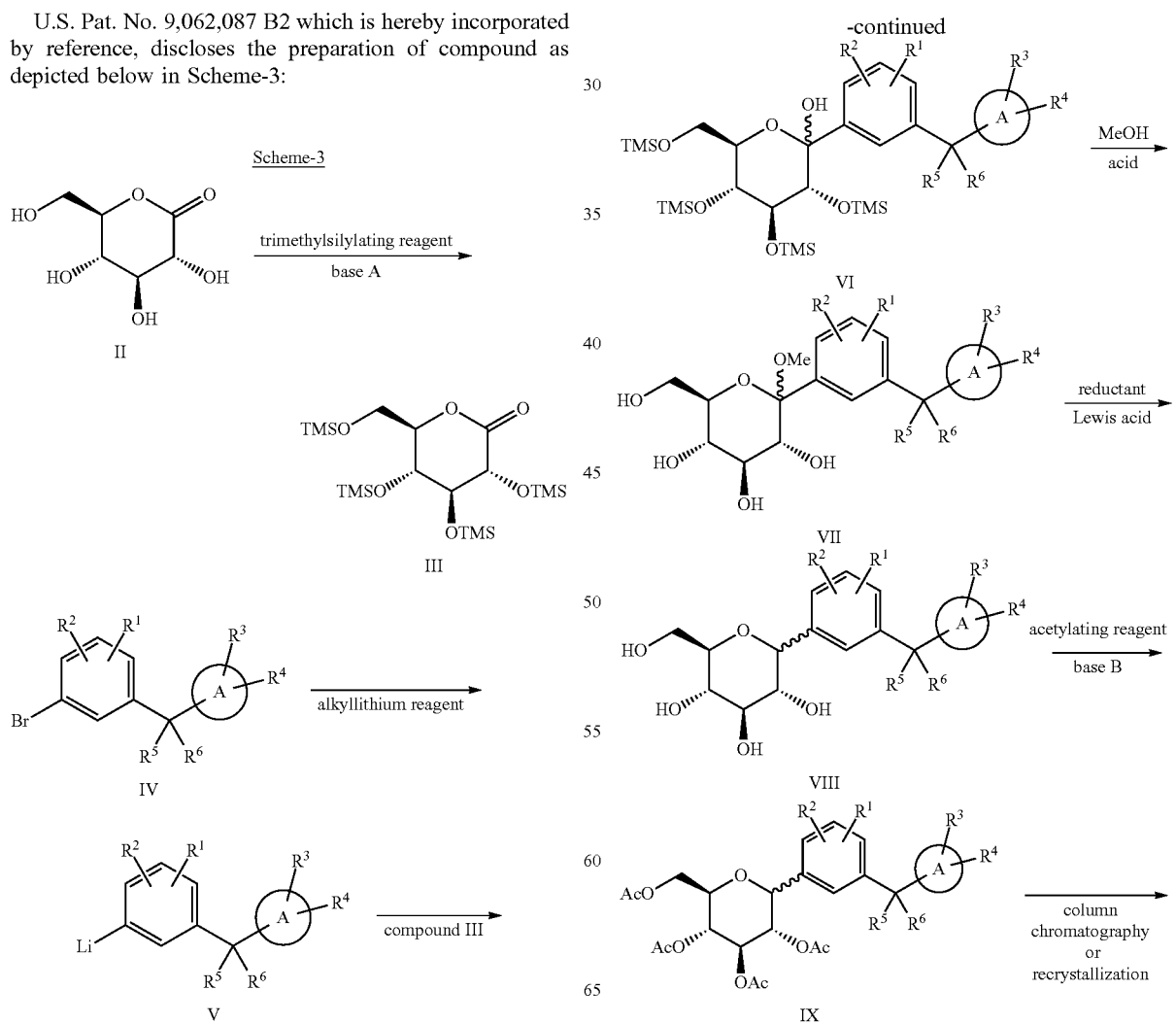

-continued

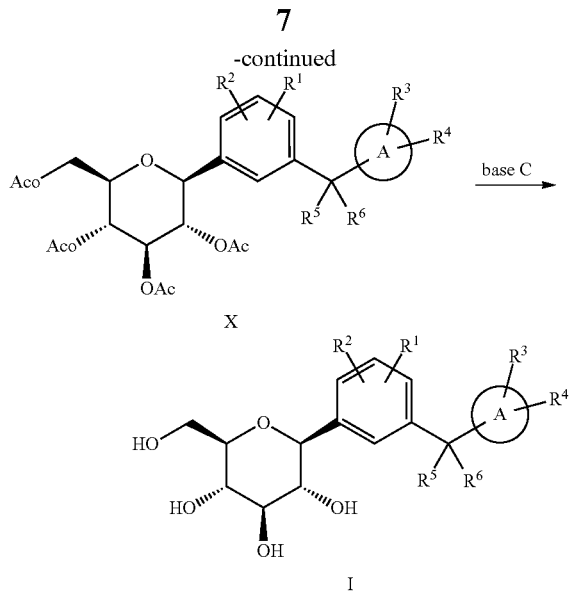

Above described processes make use of drastic reaction conditions, more unit operations; additional purification by chromatography to get high enantiomeric and chemical purity which leads to loss of yield, which is not desirable for commercial manufacturing as well as plant-scale point of view.

Existing processes are suffering from drawbacks like tedious processes, loss of yield, long reaction cycle time, more energy consumption, loss of human hours and involvement of more inventories as well as unit operations.

Inventors of the present invention have developed an improved process that addresses the problems associated with the processes reported in the prior art. The process of the present invention does not involve more unit operations. Moreover, the process does not require critical workup procedure. Accordingly, the present invention provides a process for the preparation of Bexagliflozin, which is simple, efficient, cost effective, in-situ transformation reaction, which by designing optimum conditions reduces effluent load, is environment friendly and commercially scalable for large scale operations.

SUMMARY OF THE INVENTION

In one aspect, the present invention relates to an improved process for the preparation of Bexagliflozin.

In another aspect, the present invention relates to an improved process for the preparation of Bexagliflozin, wherein Bexagliflozin compound of formula V resulted in good yield, preferably more than 70%.

In another aspect, the present invention relates to an improved process for the preparation of acetylated Bexagliflozin (formula $F^1$), wherein acetylated Bexagliflozin resulted in good overall yield, preferably more than 70%.

In another aspect, the present invention relates to an improved process for the preparation of Bexagliflozin, wherein final compound of formula V resulted in high purity, preferably >99.5%.

In another aspect, the present invention related to an improved process for the preparation of Bexagliflozin, wherein the multi-step reaction in which condensation reaction, deprotection, reduction, protection to form acetylated Bexagliflozin (formula $F^1$) are conducted in-situ by telescopic monitoring of reaction.

In another aspect, the present invention relates to a process for the preparation of acetylated Bexagliflozin (formula $F^1$), wherein purifying formed acetylated Bexagliflozin by treating with chlorinated solvent and/or alcoholic solvent or mixtures thereof to obtain acetylated Bexagliflozin of formula $F^1$ having purity greater than 99%.

In another aspect, the present invention relates to a process for the preparation of Bexagliflozin (V), wherein purifying formed Bexagliflozin by treating with aromatic hydrocarbon solvent and/or aliphatic hydrocarbon solvent and/or water or mixtures thereof to obtain Bexagliflozin (V) having purity greater than 99%.

In another aspect, the present invention relates to a process for the preparation of Bexagliflozin (V) diproline, wherein purifying formed Bexagliflozin (V) diproline by treating with aromatic hydrocarbon solvent and/or aliphatic hydrocarbon solvent and/or water or mixtures thereof to obtain Bexagliflozin (V) diproline having purity greater than 99%.

DETAILED DESCRIPTION OF THE INVENTION

In the context of the present invention, the term "mixture" means that the mixture of solvents in any suitable ratio. All alternatives are intended to be within the scope of the present invention.

All ranges recited herein include the endpoints, including those that recite a range "between" two values. Terms such as "about", "generally" and the like are to be construed as modifying a term or value such that it is not an absolute. Such terms will be defined by the circumstances and the terms that they modify as those terms are understood by those skilled in the art. This includes, at very least, the degree of expected experimental error, technique error and instrument error for a given technique used to measure a value.

The term "in-situ" typically means "in the reaction mixture" or "not in isolated form" or "existing as residue".

Accordingly, in an embodiment the present invention relates to an improved process for the preparation of Bexagliflozin represented by the following formula V and its salts, hydrates, solvates and its intermediates thereof.

Formula V

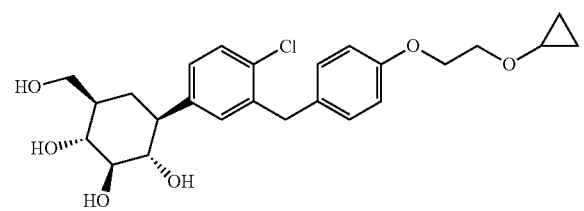

comprising following steps;
a) reacting the compound of formula $A^1$ with the compound of formula $B^1$ in suitable solvent in the presence of organolithium reagent to provide the compound of formula $C^1$;

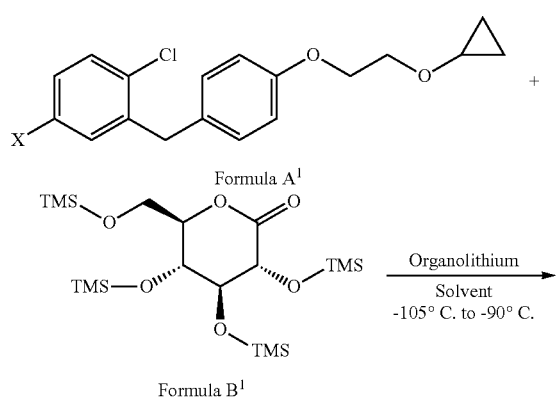
Formula A[1]
Formula B[1]
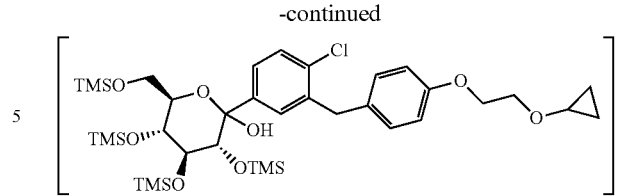
Formula C[1]
wherein, X is halo selected from F, Cl, Br, I.
b) reacting the compound of formula C[1] with methane sulphonic acid in suitable solvent in to provide the compound of formula D[1];
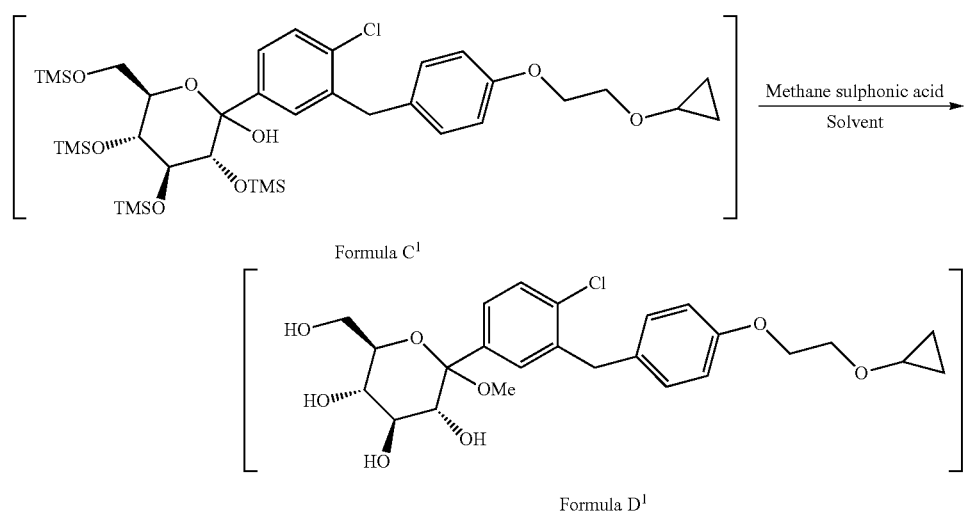
Formula C[1]
Formula D[1]
c) reacting the compound of formula D[1] with reducing agent in suitable solvent to form the compound of formula E[1];
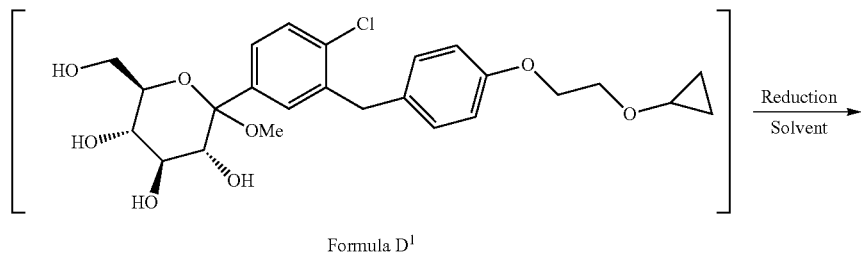
Formula D[1]
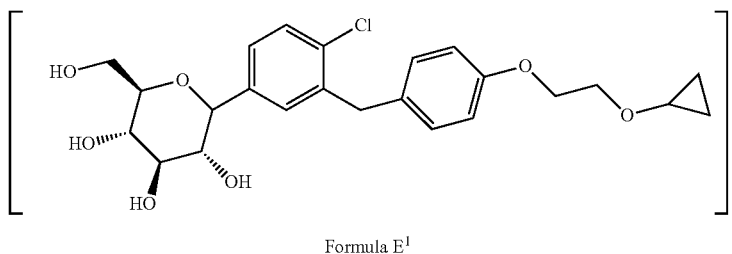
Formula E[1]

d) acetylating the compound of formula $E^1$ in the presence of acetylating reagent in suitable solvent to isolate compound of formula $F^1$.

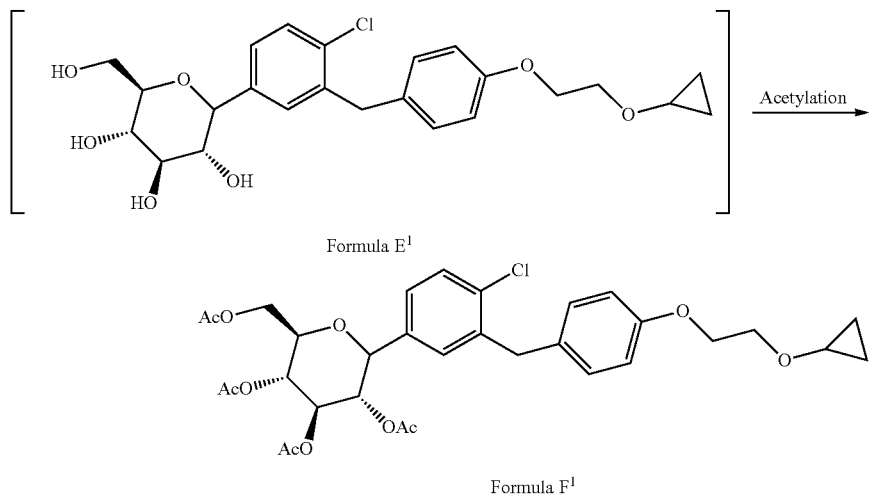

e) hydrolyzing compound of formula $F^1$ in the presence of base in suitable solvent to form Bexagliflozin of formula V; and
f) optionally converting Bexagliflozin of formula V into its hydrates, solvates or salts thereof, wherein the compounds of formula $C^1$, $D^1$ and $E^1$ are formed in-situ.

In an embodiment, the suitable solvent used in the process herein above is selected from the group comprising of water, alcohols, ethers, amides, esters, nitrites, sulfoxides, ketones, hydrocarbons and halogenated hydrocarbons; wherein alcohol is selected from the group consisting of methanol, ethanol, iso-propanol. n-butanol, iso-butanol and the like; ester is selected from the group consisting of ethyl acetate, isopropyl acetate; ketone is selected from the group consisting of acetone, methyl isobutyl ketone, methyl ethyl ketone; ether is selected from the group consisting of methyl tea-butyl ether, diisopropyl ether, diethyl ether tetrahydrofuran, 2-methyl tetrahydrofuran, cyclopentyl methyl ether, dioxane and the like; halogenated solvent is selected from the group consisting of dichloromethane, chloroform, chlorobenzene, bromobenzene and the like; hydrocarbons is selected from the group consisting of toluene, xylene, cyclohexane and the like; nitrile is selected from the group consisting of acetonitrile, propionitrile and the like; amide is selected from the group consisting of N,N-dimethylformamide, N,N-dimethyl acetamide and the like; sulfoxide such as dimethyl sulfoxide; sulfone; or mixtures thereof.

In an embodiment, organolithium reagent may be selected from n-butyllithium, sec-butyllithium, isopropyllithium, tert-butyllithium and the like.

In an embodiment, reducing agent may be mixture of triethylsilane and aluminum chloride.

In an embodiment, acetylating reagent may be selected from acetic anhydride or acetyl chloride.

In an embodiment, base may be selected from inorganic base or organic base or mixtures thereof.

In an embodiment, the organic base is selected from the group consisting of 1,8-diazabicyclo[5.4.0]undec-7-ene (DBU), 1,5-diazabicyclo[4.3.0]non-5-ene (DBN), pyridine, dimethylaminopyridine, dibutyl amine, triethyl amine, tributyl amine, diisopropyl amine, diisopropylethylamine, N-methylmorpholine and the like.

In an embodiment, the inorganic base is selected from the group consisting of hydroxides of alkali metals or alkaline earth metals such as sodium hydroxide, potassium hydroxide, lithium hydroxide, calcium hydroxide; carbonates such as sodium carbonate, potassium carbonate; bicarbonates of alkali metals or alkaline earth metals such as sodium bicarbonate, potassium bicarbonate; ammonia and the like.

In an embodiment, the Bexagliflozin (V) is converted to its diproline complex.

The main objective of the present invention is to achieve high purity and yield, simultaneously avoiding use of $BF_3$-etherate as reducing agent which always requires safety precautions.

Moreover that, recovery of compound of formula $F^1$ via in-situ transformation from compound of formula $C^1$ increases overall yield from 46% to about 60% as compared to prior art.

Accordingly, in an embodiment the present invention relates to an improved process for the preparation of acetylated Bexagliflozin of formula $F^1$,

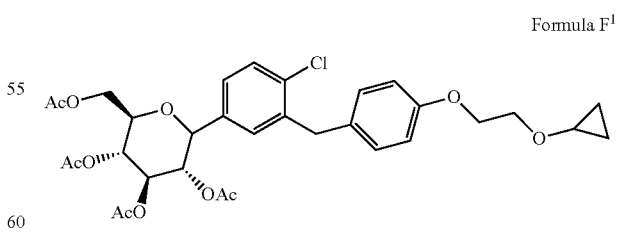

Formula $F^1$ comprising following steps;
a) reacting the compound of formula $A^1$ with the compound of formula $B^1$ in suitable solvent in the presence of organolithium reagent to provide the compound of formula $C^1$;

13
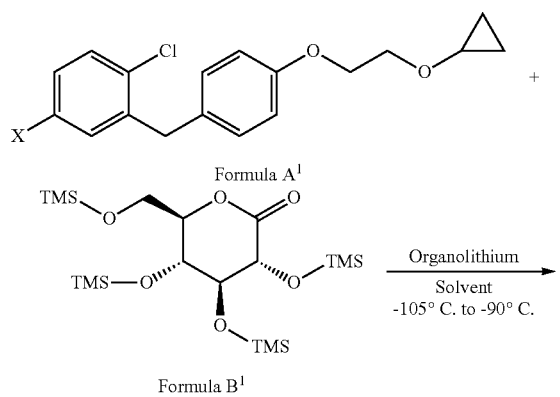
Formula A¹
Formula B¹
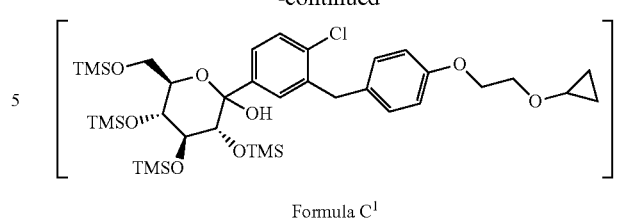
Formula C¹
wherein, X is halo selected from F, Cl, Br, I.
b) reacting the compound of formula C¹ with methane-sulphonic acid in suitable solvent to provide the compound of formula D¹;
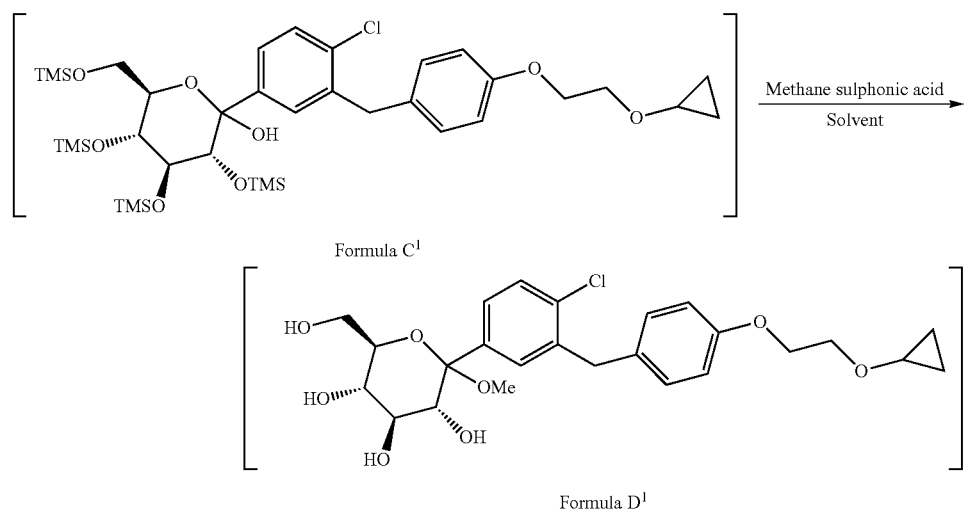
Formula C¹
Formula D¹
c) reacting the compound of formula D¹ with reducing agent in suitable solvent to form the compound of formula E¹;
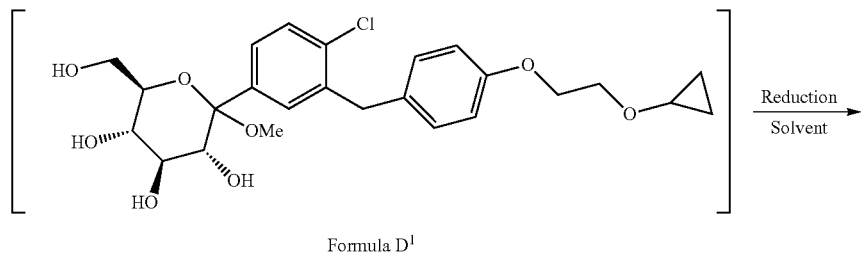
Formula D¹
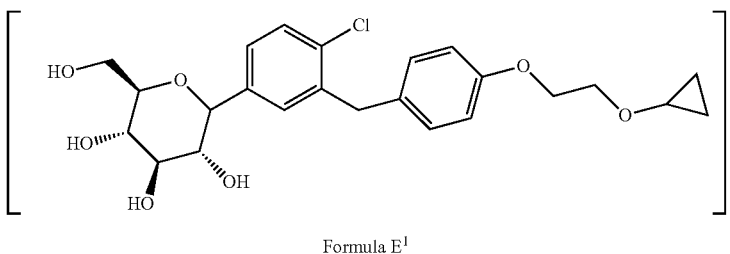
Formula E¹ d) acetylating the compound of formula E¹ in the presence of acetylating reagent in suitable solvent to isolate compound of formula F¹.

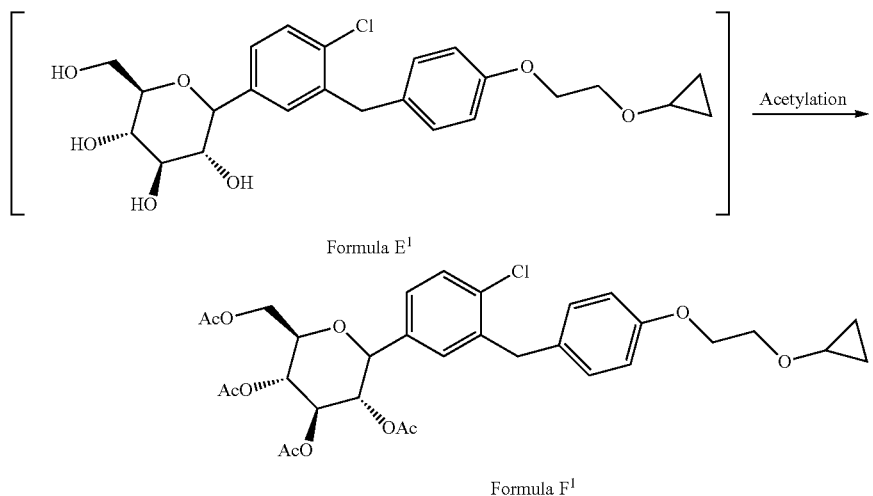

Formula E¹

Acetylation

Formula F¹ wherein the compounds of formula C¹, D¹ and E¹ are formed in-situ.

In an embodiment, the suitable solvent used in the process herein above is selected from the group comprising of water, alcohols, ethers, amides, esters, nitriles, sulfoxides, ketones, hydrocarbons and halogenated hydrocarbons; wherein alcohol is selected from the group consisting of methanol, ethanol, iso-propanol. n-butanol, iso-butanol and the like; ester is selected from the group consisting of ethyl acetate, isopropyl acetate; ketone is selected from the group consisting of acetone, methyl isobutyl ketone, methyl ethyl ketone; ether is selected from the group consisting of methyl tert-butyl ether, diisopropyl ether, diethyl ether tetrahydrofuran, 2-methyl tetrahydrofuran, cyclopentyl methyl ether, dioxane and the like; halogenated solvent is selected from the group consisting of dichloromethane, chloroform, chlorobenzene, bromobenzene and the like; hydrocarbons is selected from the group consisting of toluene, xylene, cyclohexane and the like; nitrile is selected from the group consisting of acetonitrile, propionitrile and the like; amide is selected from the group consisting of N,N-dimethylformamide, N,N-dimethyl acetamide and the like; sulfoxide such as dimethyl sulfoxide; sulfone; or mixtures thereof.

In an embodiment, organolithium reagent may be selected from n-butyllithium, sec-butyllithium, isopropyllithium, tert-butyllithium and the like.

In an embodiment, reducing agent may be mixture of triethylsilane and aluminum chloride.

In an embodiment, acetylating reagent may be selected from acetic anhydride or acetyl chloride.

Accordingly, in an embodiment the present invention relates to a process for the preparation of formula C¹, comprising the step of: reacting the compound of formula A¹ with the compound of formula B¹ in suitable solvent in the presence of organolithium reagent to provide the compound of formula C¹, wherein reaction is preferably conducted at the temperature –105° C. to –90° C.

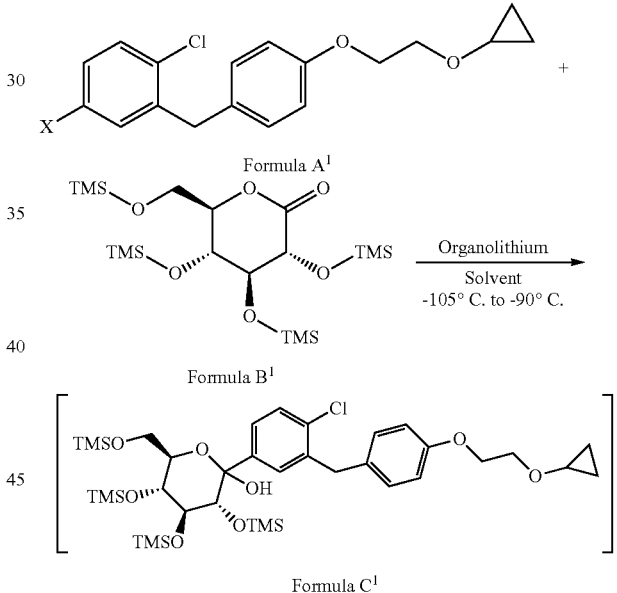

Formula A¹

Formula B¹

Formula C¹ wherein, X is halo selected from F, Cl, Br, I.

Surprisingly, it has been found that, in the preparation of formula C¹, the reaction temperature has critical role, which gives better reaction profile in terms of significantly reduced impurities such as dimer impurity and ultimately gives better yield and purity as compared to prior art.

Accordingly, in an embodiment the present invention relates to a process for the preparation of acetylated Bexagliflozin of formula F¹, wherein purifying formed acetylated Bexagliflozin by treating with halogenated solvent and/or alcohol or mixtures thereof to obtain acetylated Bexagliflozin of formula F¹ having purity greater than 99%.

In an embodiment, the suitable solvent used in the process herein above is selected from the group comprising of water, alcohols, halogenated hydrocarbons; or mixtures thereof, wherein alcohol is selected from the group consisting of methanol, ethanol, iso-propanol. n-butanol, iso-butanol and the like; halogenated solvent is selected from the group consisting of dichloromethane, chloroform, chlorobenzene, bromobenzene and the like.

The significant advantages of the present invention is to provide purer compound of formula $F^1$ by treating with halogenated solvent and/or alcohol or mixtures thereof to control the following impurities less than 0.1%. Hence there is no specific purification requirement of final Bexagliflozin of formula V as impurities can be controlled at formation of formula $F^1$.

1) Dimer of starting material of formula $A^1$

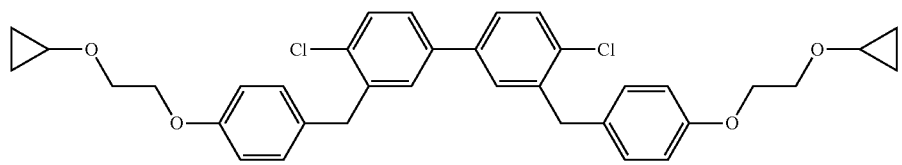 [SMILES: Clc1ccc(-c2ccc(Cl)c(Cc3ccc(OCCOC4CC4)cc3)c2)cc1Cc1ccc(OCCOC2CC2)cc1]

2) Dimer of Acetyl derivative of Bexagliflozin

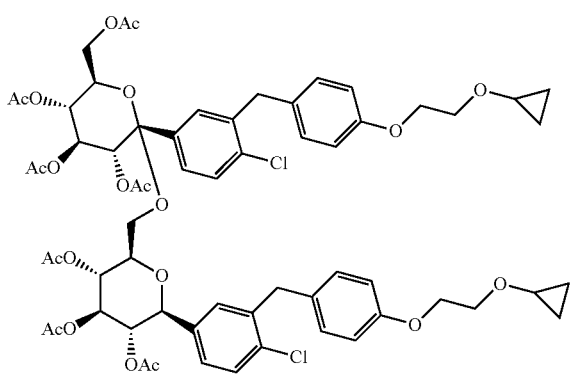 [SMILES: CC(=O)OC[C@H]1O[C@@](OC[C@H]2O[C@@H](c3ccc(Cl)c(Cc4ccc(OCCOC5CC5)cc4)c3)[C@H](OC(C)=O)[C@@H](OC(C)=O)[C@@H]2OC(C)=O)(c2ccc(Cl)c(Cc3ccc(OCCOC4CC4)cc3)c2)[C@H](OC(C)=O)[C@@H](OC(C)=O)[C@@H]1OC(C)=O]

3) Alpha isomer of acetyl derivative of Bexagliflozin.

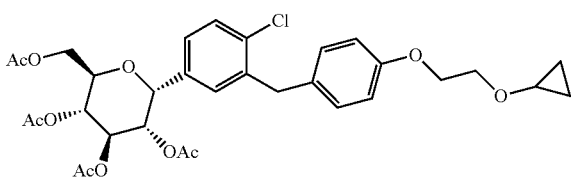 [SMILES: CC(=O)OC[C@H]1O[C@H](c2ccc(Cl)c(Cc3ccc(OCCOC4CC4)cc3)c2)[C@H](OC(C)=O)[C@@H](OC(C)=O)[C@@H]1OC(C)=O]

4) Methoxy tetra acetate impurity.

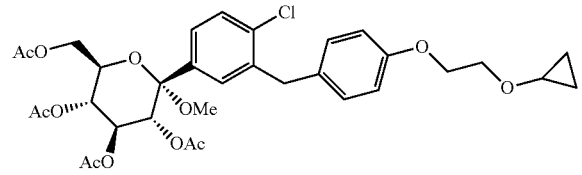 [SMILES: CO[C@@]1(c2ccc(Cl)c(Cc3ccc(OCCOC4CC4)cc3)c2)O[C@H](COC(C)=O)[C@@H](OC(C)=O)[C@H](OC(C)=O)[C@H]1OC(C)=O]

In an embodiment, there is provided pure Bexagliflozin (V) substantially free of compounds selected from dimer of starting material of formula A1, dimer of Acetyl derivative of Bexagliflozin, alpha isomer of acetyl derivative of Bexagliflozin, methoxy tetra acetate impurity.

In an embodiment, there is provided pure Bexagliflozin (V) substantially free of compounds selected from dimer of starting material of formula $A^1$, dimer of Acetyl derivative of Bexagliflozin, alpha isomer of acetyl derivative of Bexagliflozin, methoxy tetra acetate impurity; wherein overall impurities are less than 0.1%.

In an embodiment, there is provided pure acetylated Bexagliflozin compound of formula $F^1$ substantially free of compounds selected from dimer of starting material of formula A1, dimer of Acetyl derivative of Bexagliflozin, alpha isomer of acetyl derivative of Bexagliflozin, methoxy tetra acetate impurity.

In an embodiment, there is provided pure acetylated Bexagliflozin compound of formula $F^1$ substantially free of compounds selected from dimer of starting material of formula A1, dimer of Acetyl derivative of Bexagliflozin, alpha isomer of acetyl derivative of Bexagliflozin, methoxy tetra acetate impurity; wherein overall impurities are less than 0.1%.

Accordingly, in an embodiment the present invention relates to a process for the preparation of Bexagliflozin (V), wherein purifying formed Bexagliflozin by treating with aromatic hydrocarbon solvent and/or aliphatic hydrocarbon solvent and/or water or mixtures thereof to obtain Bexagliflozin of formula V or its proline complex (salt) having purity greater than 99%.

In an embodiment, the suitable solvent used in the process herein above is selected from the group comprising of water, hydrocarbons; wherein hydrocarbons is selected from the group consisting of aromatic hydrocarbon such as toluene, xylene, aliphatic hydrocarbon such as cyclohexane, n-hexane and the like; or mixtures thereof.

Accordingly, in an embodiment the present invention relates to a process for the preparation of Bexagliflozin of formula V, wherein purifying formed Bexagliflozin by treating with suitable solvent or mixture of solvents or by crystallization or by solvent-antisolvent treatment to provide Bexagliflozin of formula V having purity greater than 99%.

The process of the present invention as per the specific embodiment described above is illustrated in the following Scheme-4,

Scheme-4

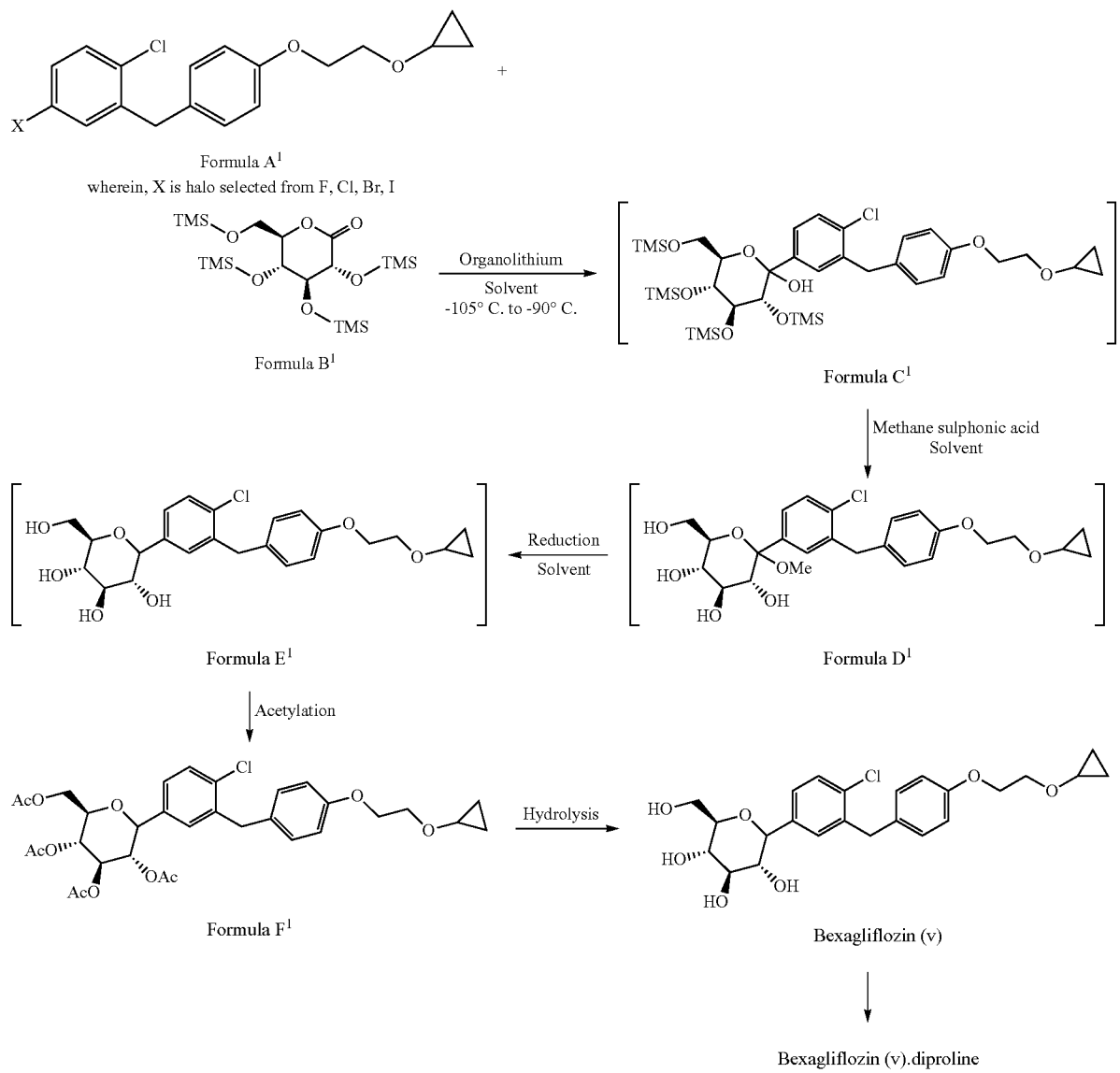

The invention is further illustrated by the following examples which are provided to be exemplary of the invention, and do not limit the scope of the invention. While the present invention has been described in terms of its specific embodiments, certain modifications and equivalents will be apparent to those skilled in the art and are intended to be included within the scope of the present invention.

EXAMPLES

Example-1: Preparation of Acetylated Bexagliflozin (Formula $F^1$)

To the solution of 1-chloro-2-(4-(2-cyclopropoxyethoxy) benzyl)-4-iodobenzene in tetrahydrofuran, n-BuLi (2.5 mol) in hexane is added at a rate that maintains the reaction temperature below −90° C. followed by addition of 2,3,4, 6-tetra-O-trimethylsilyl-β-D-glucolactone in toluene at a rate to maintain the reaction temperature below −90° C. The solution is stirred for 30 min at −95° C. prior to quenching by addition of methanol containing methanesulfonic acid. The reaction mass is stirred till completion of reaction at 25° C. to 35° C. After completion of reaction, the reaction is quenched by the addition of triethylamine and distilled out under vacuum. To the obtained residue water is added and extracted with ethylacetate. The combined ethylacetate fractions are washed with brine and dried over sodium sulfate. The reaction mixture is concentrated to provide compound of formula $D^1$. To the methylenechloride solvent, aluminum chloride is added in one lot and cooled the mass to the temperature 0° C. to 10° C. To the prepared solution acetonitrile is added followed by addition of triethyl silane at a rate such that the temperature is maintained between 0° C. to 10° C. Mixed the above prepared complex with compound of formula $D^1$ and stirred for about 2 h. When HPLC analysis revealed that the reaction was completed, the reaction is quenched by addition of 50% aqueous hydrochloric acid solution. Aqueous layer is extracted with methylenechloride. Combined organic layer is washed with 5% aqueous hydrochloric acid solution followed by water and brine. The organic layer is distilled and to the obtained residue is added methylenechloride, acetic anhydride and dimethylaminopyridine, pyridine and stirred for 5-6 h. Water is added to the reaction mixture and layers are separated. The methylenechloride layer is distilled and ethanol is added to it followed by heating to 55-60° C. The reaction mixture is cooled, filtered and dried to give acetylated Bexagliflozin of formula Yield: ~58%; Purity (by HPLC): ≥99.8%

Example-2: Preparation of Bexagliflozin (Formula V)

To the solution of methanol (250 mL), water (25 mL) and sodium hydroxide (4 mol), acetylated bexagliflozin is added at temperature 25-35° C. The reaction mixture is flushed with methanol (50 mL) and stirred for 10-15 minutes followed by maintaining the reaction mixture at 60-70° C. for 2 hours. The reaction mixture is then cooled to 25-35° C. and acetic acid (5 mL) is added into it at 25-35° C. to adjust the pH 6.5-8.0. Isopropyl acetate (250 mL) and water (300 mL) are added into the reaction mixture at temperature 25-35° C. and stirred for 15-20 minutes followed by separating the layers. Aqueous layer is extracted with Isopropyl acetate (100 mL). The organic layer is washed with demineralized water (250 mL) followed by charcoal treatment. The solvent is distilled under vacuum at below 55° C. up to 2.5 to 3.5 volumes. The reaction mixture is then cooled to 25-35° C. and water (15 mL) is added and stirred at 25-30° C. for 30-45 minutes. To the reaction mixture is then added cyclohexane (250 mL) at 25-30° C. and stirred at 25-30° C. for 12-15 hours. The product is filtered under vacuum at 25-30° C. and the product is washed with cyclohexane (100 mL) and dried the material under vacuum 50-55° C. till water and residual solvents comes under limit to obtain Bexagliflozin. Yield: ~90%; Purity (by HPLC): ≥99.9%. This may be further treated with L-Proline to obtain Bexagliflozin (V) diproline.

We claim:

1. A process for the preparation of Bexagliflozin (I) or its salts, hydrates, solvates and its intermediates thereof, Formula V

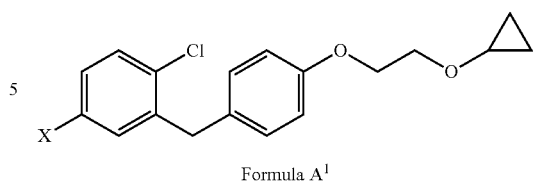

comprising following steps;

a) reacting the compound of formula A¹ with the compound of formula B¹ in a solvent at temperature ranging between −105° C. to −85° C. in the presence of organolithium reagent, selected from the group consisting of n-butyllithium, sec butyllithium, isopropyllithium and tert-butyllithium, to provide the compound of formula C¹;

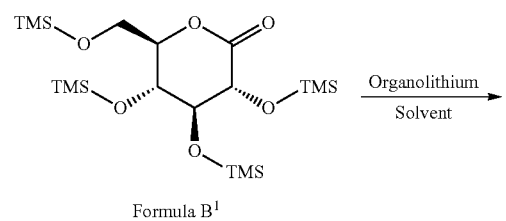

Formula A¹

Formula B¹

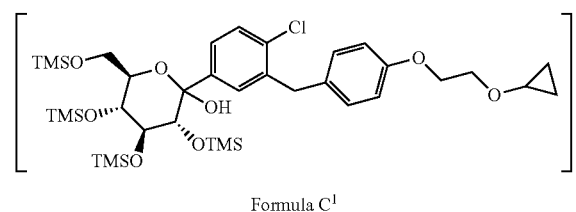

Formula C¹ wherein, X is halo selected from F, Cl, Br, I;

b) reacting the compound of formula C¹ with methanesulphonic acid in a solvent to provide the compound of formula D¹;

Formula C¹

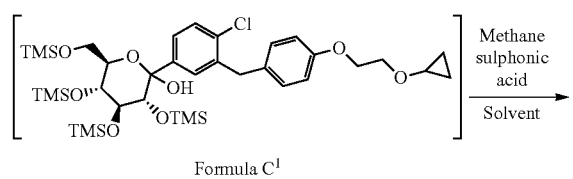

Formula D¹ c) reacting the compound of formula D¹ with reducing agent, which is a mixture of triethyl silane and aluminium chloride, in a solvent to form the compound of formula E¹;

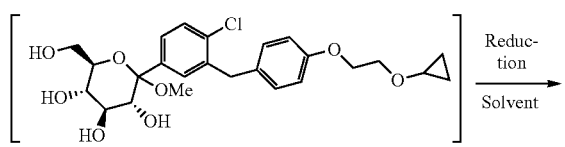

Formula D¹

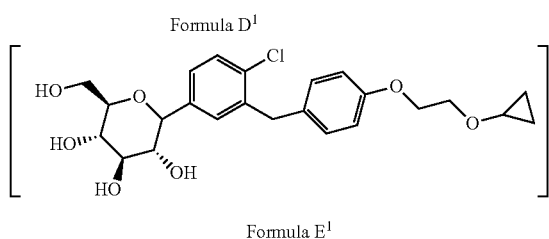

Formula E¹ d) acetylating the compound of the formula E¹ in the presence of acetylating reagent, selected from acetic anhydride or acetyl chloride, in a solvent to isolate compound of formula F¹;

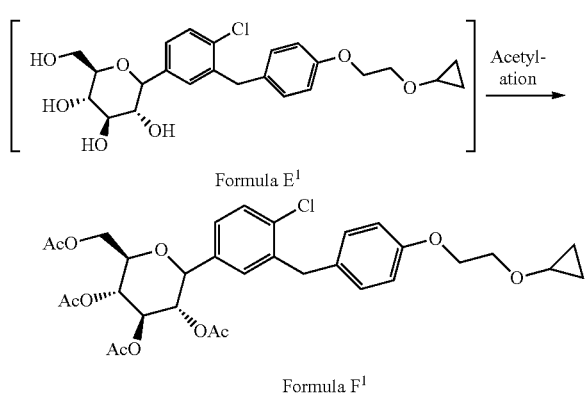

e) hydrolyzing compound of Formula F¹ in the presence of base in alcohol and isolating with ester to form Bexagliflozin of formula V; and f) optionally converting Bexagliflozin of formula V into its hydrates, solvates or salts thereof, wherein the compounds of formula C¹, D¹ and E¹ are formed in-situ.

2. The process according to claim 1, wherein the compound of formula F¹ is treated with halogenated solvent, alcohol solvent, water; or mixtures thereof, to yield pure acetylated Bexagliflozin of formula F¹ having impurities less than 0.1%.

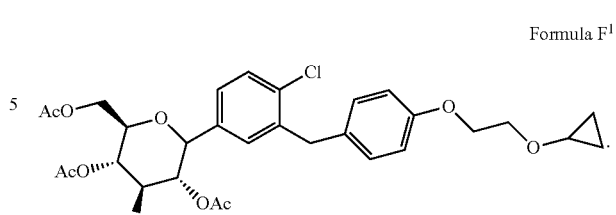

Formula F¹

3. The process according to claim 2, wherein pure acetylated Bexagliflozin of formula F¹ is obtained, having purity greater than 99%.

4. The process according to claim 2, wherein the alcohol solvent is selected from the group consisting of methanol, ethanol, iso-propanol, n-butanol and iso-butanol; and the halogenated solvent is selected from the group consisting of dichloromethane, chloroform, chlorobenzene and bromobenzene.

5. The process according to claim 1, wherein the Bexagliflozin obtained in step (e) is purified by treating with aromatic hydrocarbon solvent and/or aliphatic hydrocarbon solvent and/or water, or mixtures thereof; to obtain pure Bexagliflozin of formula V having purity greater than 99%.

6. The process according to claim 5, wherein the aromatic hydrocarbon solvent is selected from the group consisting of toluene and xylene; and aliphatic hydrocarbon solvent is selected from the group consisting of cyclohexane and n-hexane.

7. The process according to claim 5, wherein pure Bexagliflozin (V) obtained is substantially free of compounds selected from dimer of formula A¹, dimer of Acetyl derivative of bexagliflozin, alpha isomer of acetyl derivative of Bexagliflozin and methoxy tetra acetate impurity Dimer of Formula A¹

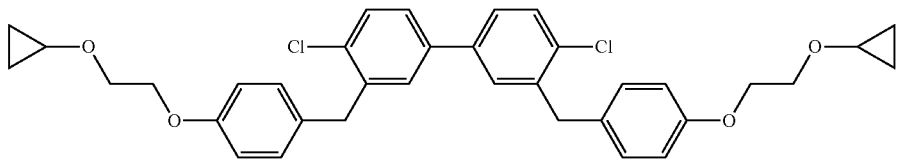 [SMILES: Clc1ccc(-c2ccc(Cl)c(Cc3ccc(OCCOC4CC4)cc3)c2)cc1Cc1ccc(OCCOC2CC2)cc1]

Dimer of Acetyl derivative of Bexagliflozin

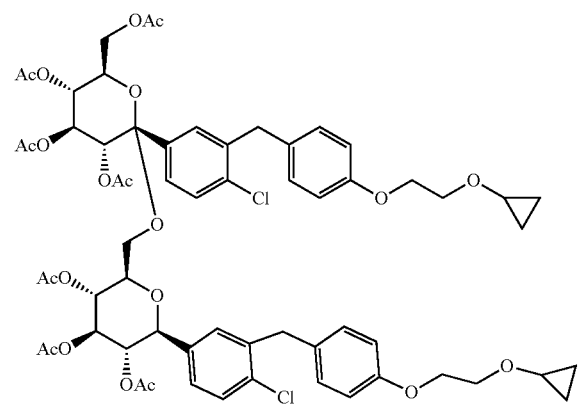 [SMILES: CC(=O)OC[C@H]1O[C@@](OC[C@H]2O[C@@H](c3ccc(Cl)c(Cc4ccc(OCCOC5CC5)cc4)c3)[C@H](OC(C)=O)[C@@H](OC(C)=O)[C@@H]2OC(C)=O)(c2ccc(Cl)c(Cc3ccc(OCCOC4CC4)cc3)c2)[C@H](OC(C)=O)[C@@H](OC(C)=O)[C@@H]1OC(C)=O]

Alpha isomer of acetyl derivative of Bexagliflozin,
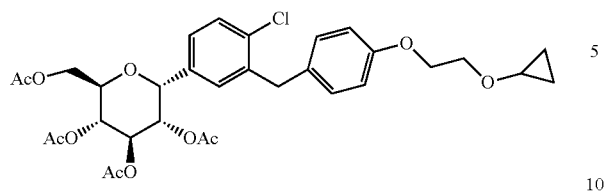
Methoxy tetra acetate impurity
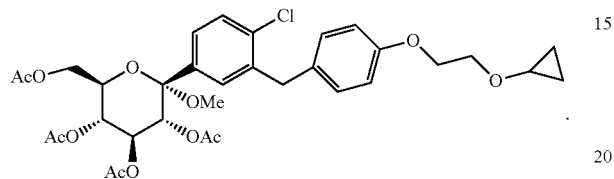
8. The process according to the claim 7, wherein the pure Bexagliflozin (V) is obtained having impurities less than 0.1%.
* * * * *